US00PP15067P2

(12) United States Plant Patent
Oliver

(10) Patent No.: US PP15,067 P2
(45) Date of Patent: Aug. 3, 2004

(54) HEUCHERA PLANT NAMED 'SILVER LIGHT'

(50) Latin Name: ***Heuchera* sp.**
Varietal Denomination: Silver Light

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 5 days.

(21) Appl. No.: 10/324,932

(22) Filed: Dec. 20, 2002

(51) Int. Cl.[7] ..... A01H 5/00

(52) U.S. Cl. ..... Plt./263

(58) Field of Search ..... Plt./263

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of Heuchera plant named 'Silver Light', characterized by its full, densely foliated and uniformly mounded plant habit; upper surfaces of leaves silver in color; lower leaf surfaces dark purple in color; numerous showy pink-colored flowers arranged on erect panicles; and excellent garden performance.

2 Drawing Sheets

Botanical classification/cultivar designation: Heuchera sp. cultivar Silver Light.

BACKGROUND OF THE INVENTION

The present invention relates to a new and distinct cultivar of Heuchera plant, botanically known as Heuchera sp. and hereinafter referred to by the name 'Silver Light'.

The new Heuchera is a product of a planned breeding program conducted by the Inventor in Scottdale, Pa. The objective of the breeding program is to create new Heuchera cultivars having good plant vigor, dense and uniform plant habit, and showy and attractive flower and leaf coloration.

The new Heuchera was discovered by the Inventor in a controlled environment in Scottdale, Pa., from seedling progeny from a self-pollination made by the Inventor in May, 1998, of the Heuchera cultivar Silver Maps, not patented. The new Heuchera was selected by the Inventor in May, 1999. The selection of this plant was based on its desirable flower and foliage coloration.

Asexual reproduction of the new Heuchera by cuttings taken in a controlled environment in Scottdale, Pa., since August, 1999, has shown that the unique features of this new Heuchera are stable and reproduced true to type in successive generations.

SUMMARY OF THE INVENTION

The cultivar Silver Light has not been observed under all possible environmental conditions. The phenotype may vary somewhat with variations in environment such as temperature and light intensity, without, however, any variance in genotype.

The following traits have been repeatedly observed and are determined to be the unique characteristics of 'Silver Light'. These characteristics in combination distinguish 'Silver Light' as a new and distinct cultivar of Heuchera:

1. Full, densely foliated and uniformly mounded plant habit.
2. Upper surfaces of leaves silver in color; lower leaf surfaces dark purple in color.

3. Numerous showy pink-colored flowers arranged on erect panicles.
4. Excellent garden performance.

Plants of the new Heuchera can be compared to plants of the parent, the cultivar Silver Maps. In side-by-side comparisons conducted by the Inventor in Scottdale, Pa., plants of the new Heuchera differed from plants of the cultivar Silver Maps in the following characteristics:

1. Leaves of plants of the new Heuchera were more silvery in color than leaves of plants of the cultivar Silver Maps.
2. Inflorescences of plants of the new Heuchera were shorter than inflorescences of plants of the cultivar Silver Maps.
3. Flowers of plants of the new Heuchera were pink in color whereas flowers of plants of the cultivar Silver Maps were white shaded with pink in color.

Plants of the new Heuchera can be compared to plants of the cultivar Silver Scrolls, disclosed in U.S. Plant Pat. No. 12,066. In side-by-side comparisons conducted by the Inventor in Scottdale, Pa., plants of the new Heuchera differed from plants of the cultivar Silver Scrolls in the following characteristics:

1. Leaves of plants of the new Heuchera were more sharply lobed than leaves of plants of the cultivar Silver Scrolls.
2. Leaves of plants of the new Heuchera had more extensive venation than leaves of plants of the cultivar Silver Scrolls.
3. Inflorescences of plants of the new Heuchera were shorter than inflorescences of plants of the cultivar Silver Scrolls.
4. Flowers of plants of the new Heuchera were pink in color whereas flowers of plants of the cultivar Silver Scrolls were white in color.

Plants of the new Heuchera can also be compared to plants of the cultivar Jade Gloss, disclosed in U.S. Plant Pat. No. 13,137. In side-by-side comparisons conducted by the Inventor in Scottdale, Pa., plants of the new Heuchera differed from plants of the cultivar Jade Gloss in the following characteristics:

1. Leaves of plants of the new Heuchera were more silvery in color than leaves of plants of the cultivar Jade Gloss.
2. Leaves of plants of the new Heuchera were flat whereas leaves of plants of the cultivar Jade Gloss were cupped.
3. Flowers of plants of the new Heuchera were pink in color whereas flowers of plants of the cultivar Jade Gloss were white shaded with pink in color.

BRIEF DESCRIPTION OF THE PHOTOGRAPHS

The accompanying colored photographs illustrate the overall appearance of the new Heuchera, showing the colors as true as it is reasonably possible to obtain in colored reproductions of this type. Colors in the photographs may differ slightly from the color values cited in the detailed botanical description which accurately describe the colors of the new Heuchera.

The photograph on the first sheet comprises a side perspective view of a typical one-year old flowering plant of 'Silver Light'.

The photograph on the second sheet is a close-up view of a typical inflorescence of 'Silver Light'.

DETAILED BOTANICAL DESCRIPTION

In the following description, color references are made to The Royal Horticultural Society Colour Chart, 1995 Edition, except where general terms of ordinary dictionary significance are used. The following detailed botanical description describes plants grown in Scottdale, Pa. during the summer in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C.

Botanical classification: Heuchera sp. cultivar Silver Light.

Parentage: Self-pollination of Heuchera sp. cultivar Silver Maps, not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and white in color.

*Rooting habit.*—Freely branching.

Plant description:

*Appearance.*—Perennial; basal rosette plant habit with leaves developing from the base; densely foliated; full, mounded and uniform plant habit with upright panicles with pink-colored flowers. Vigorous and robust growth habit.

*Plant size.*—Height, soil level to top of foliar plane: About 10 to 12 cm. Height, soil level to top of panicles: About 30 to 40 cm. Diameter or spread: About 40 to 45 cm.

*Foliage description.*—Arrangement: Basal rosette, simple. Length: About 7 cm. Width: About 6.5 cm. Shape: Cordate to rounded; seven-lobed, lobes acute. Apex: Obtuse. Base: Auriculate to cordate. Margin: Crenate with fine ciliation. Texture, upper surface: Glabrous; slightly rough. Texture, lower surface: Slightly pubescent; slightly rough. Venation pattern: Palmate, reticulate. Color: Developing leaves, upper surface: 198C underlain with 187C. Developing leaves, lower surface: 187C. Fully expanded leaves, upper surface: 198C. Fully expanded leaves, lower surface: 187C. Venation, upper surface: 197A. Venation, lower surface: 187C. Petiole: Length: About 9 cm. Diameter: About 2 mm. Texture, upper and lower surfaces: Pubescent. Color, upper and lower surfaces: 187D underlain with 197C.

Flower description:

*Appearance/arrangement.*—Single campanulate flowers arranged on numerous erect panicles; about 150 to 300 flowers and flower buds per flowering stem. Flowers face outward to slightly upright. Flowering continuous. Flowers persistent. Flowers not fragrant.

*Time of flowering.*—Plants flower from June to July in Scottdale, Pa.

*Inflorescence longevity.*—Individual inflorescences last about one week on the plant.

*Inflorescence size.*—Length: About 30 to 40 cm. Diameter: About 7 to 8 cm.

*Flower size.*—Diameter: About 5 mm. Depth (height): About 7 mm.

*Flower buds.*—Height: About 4 mm. Diameter: About 2 mm. Shape: Bulbous. Color, at stage of showing color: 57B.

*Sepals.*—Quantity/arrangement: Five sepals, radially symmetrical and fused at base. Calyx length: About 5 mm. Calyx diameter: About 5 mm. Shape: Elongate. Apex: Obtuse. Margin: Entire. Texture, upper and lower surfaces: Pubescent. Color, when opening and fully opened, upper and lower surfaces: 57C.

*Petals.*—Quantity/arrangement: Five minute petals; radially symmetrical. Length: About 3.5 mm. Width: About 1.2 mm. Shape: Spatulate. Apex: Obtuse. Margin: Dentate. Texture, upper and lower surfaces: Pubescent. Color, when opening and fully opened, upper surface: Close to 155D. Color, when opening and fully opened, lower surface: Close to 155D; with glandular hairs, 57D in color.

*Flower bracts.*—Length: About 1.2 to 1.5 mm. Width: About 0.2 mm. Shape: Lanceolate. Apex: Acute. Margin: Entire with ciliation. Texture, upper and lower surfaces: Pubescent. Color, upper and lower surfaces: 187C underlain with 197C.

*Peduncle.*—Strength: Strong. Aspect: Upright. Length: About 20 to 25 cm. Diameter: About 3 mm. Texture: Smooth. Color: 187C underlain with 197C.

*Pedicels.*—Strength: Strong. Aspect: About 60° from vertical. Length: About 3 mm. Diameter: About 0.2 mm. Texture: Pubescent. Color: 187C underlain with 197C.

Reproductive organs:

*Androecium.*—Stamen number: Five per flower. Anther shape: Bi-lobed. Anther size: About 0.3 mm by 0.4 mm. Anther color: 31B. Amount of pollen: Moderate. Pollen color: 14B.

*Gynoecium.*—Pistil number: Two per flower. Pistil length: About 5 mm. Stigma shape: Round. Stigma color: 150D. Style length: About 3 mm. Style color: 150D. Ovary color: 150D.

Seed:

*Size.*—About 0.3 mm by 0.6 mm.

*Color.*—Close to 202A.

Disease/pest resistance: Resistance to pathogens and pests common to Heuchera has not been observed on plants grown under commercial conditions.

Weather/temperature tolerance: Plants of the new Heuchera have been observed to have excellent garden performance. Plants of the new Heuchera have demonstrated good tolerance to rain, wind, night temperatures as low as −35° C., and day temperatures as high as 45° C.

It is claimed:

1. A new and distinct cultivar of Heuchera plant named 'Silver Light', as illustrated and described.

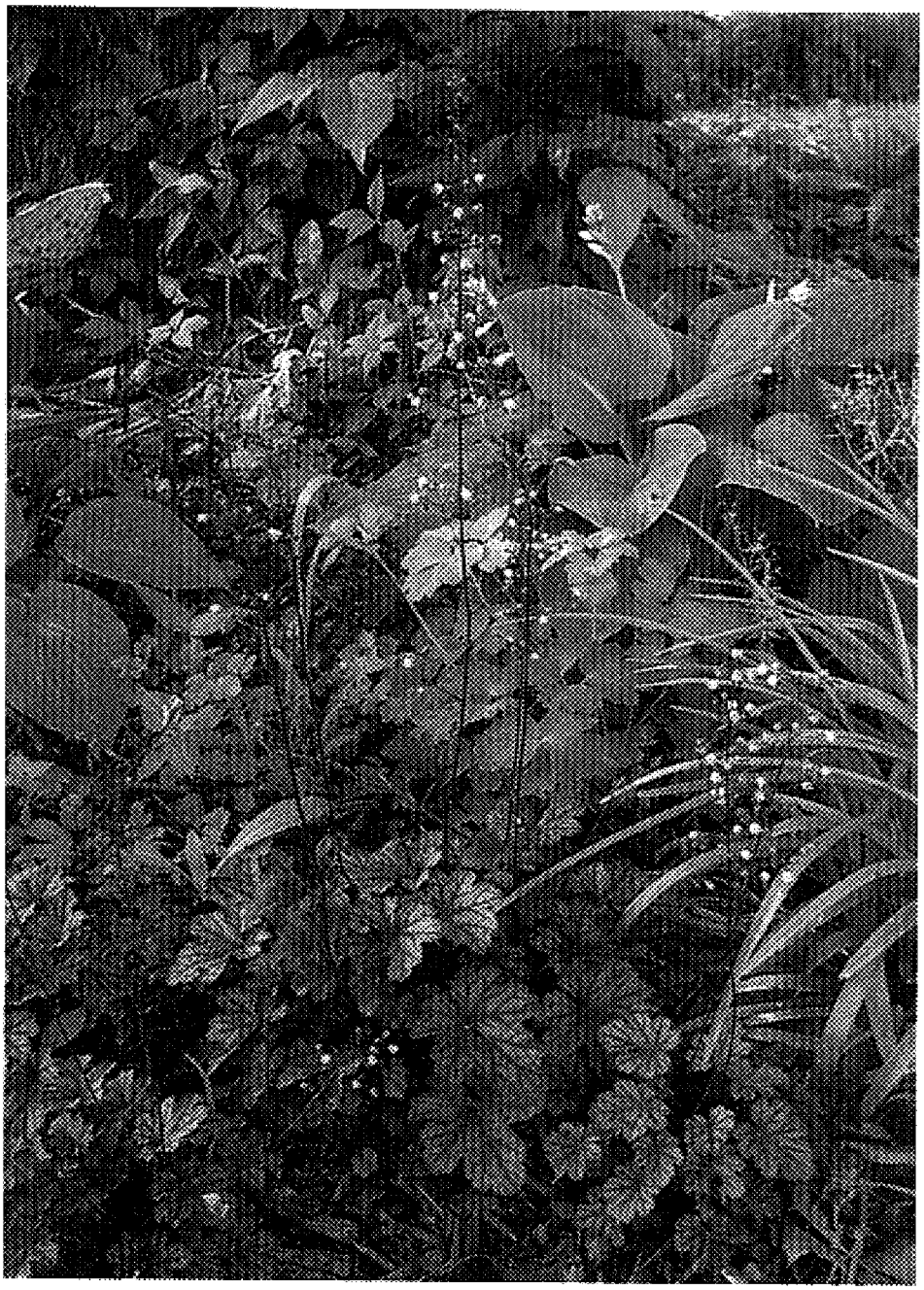

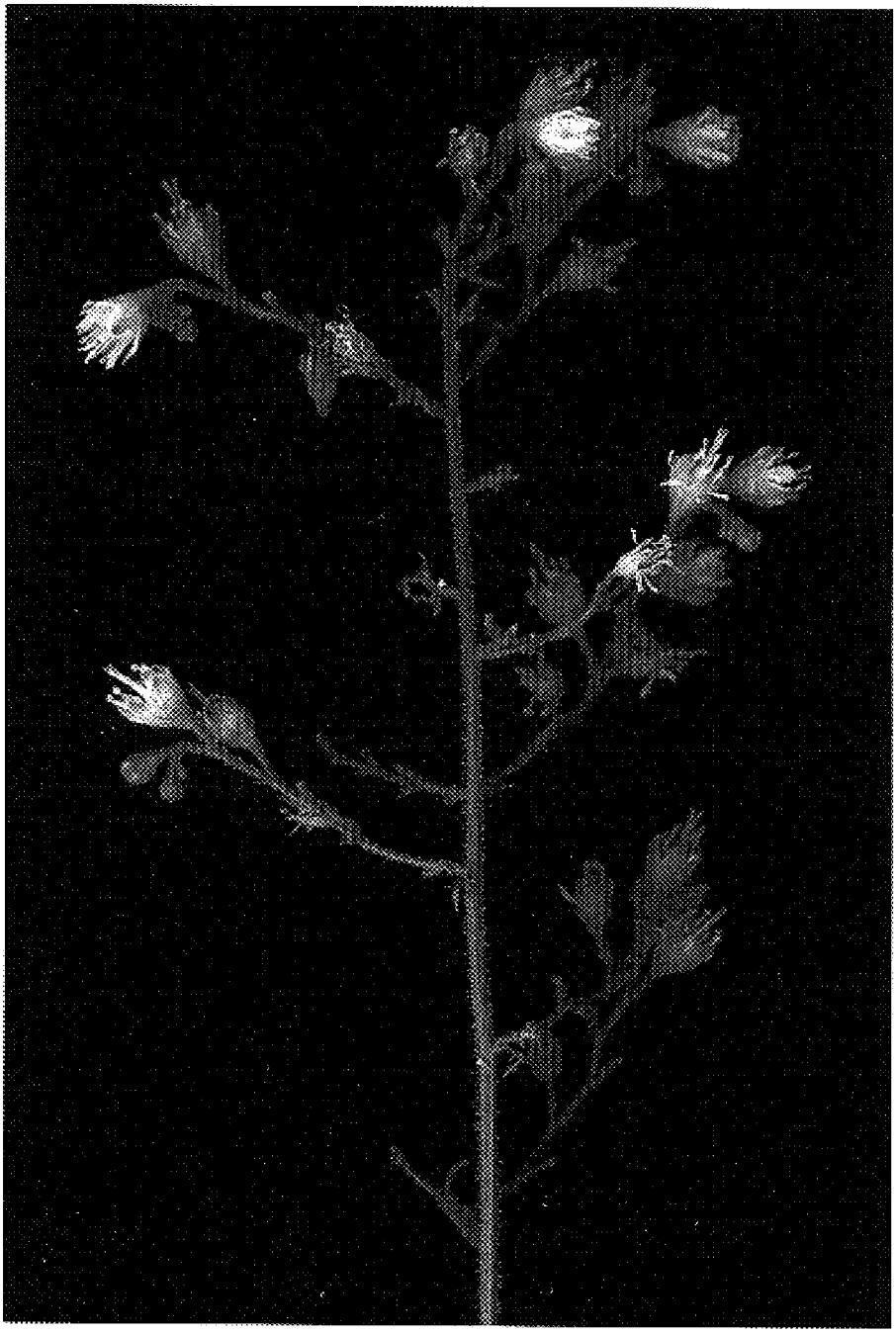

* * * * *